(12) United States Patent
Stefánsson

(10) Patent No.: US 12,161,570 B2
(45) Date of Patent: Dec. 10, 2024

(54) POWERED PROSTHETIC KNEE WITH BATTERY RECHARGING DURING REGENERATION PHASE

(71) Applicant: Össur Iceland ehf, Reykjavík (IS)

(72) Inventor: Gauti Stefánsson, Reykjavik (IS)

(73) Assignee: Össur Iceland ehf, Reykjavík (IS)

( * ) Notice: Subject to any disclaimer, the term of this patent is extended or adjusted under 35 U.S.C. 154(b) by 0 days.

(21) Appl. No.: 16/216,269

(22) Filed: Dec. 11, 2018

(65) Prior Publication Data

US 2019/0175368 A1    Jun. 13, 2019

Related U.S. Application Data

(60) Provisional application No. 62/597,658, filed on Dec. 12, 2017.

(51) Int. Cl.
*A61F 2/70* (2006.01)
*A61B 5/00* (2006.01)
(Continued)

(52) U.S. Cl.
CPC ............. *A61F 2/70* (2013.01); *A61B 5/112* (2013.01); *A61B 5/4851* (2013.01);
(Continued)

(58) Field of Classification Search
CPC .............................................. A61F 2002/708
See application file for complete search history.

(56) References Cited

U.S. PATENT DOCUMENTS 9,381,099 B2 *    7/2016 Perry ..................... A61F 2/54
2005/0105226 A1 *    5/2005 Bedard ................. H02J 7/345
361/62
(Continued)

FOREIGN PATENT DOCUMENTS

DE    102016114075         11/2017
DE    102016114075 B3     11/2017
(Continued)

OTHER PUBLICATIONS

PCT International Written Opinion and Search Report, re PCT App. No. PCT/US2018/065018, dated Mar. 28, 2019.
(Continued)

*Primary Examiner* — David H Willse
(74) *Attorney, Agent, or Firm* — Knobbe Martens Olson & Bear LLP

(57) ABSTRACT

Battery operated prostheses and systems having increased energy efficiency are disclosed. A prosthesis includes a first and second limb member coupled to an actuator to form a joint. The prosthesis further includes a rechargeable battery electrically coupled to the actuator. The actuator uses energy received from the rechargeable battery to actuate the first limb member relative to the second limb member. During at least a portion of a gait cycle of a wearer of the prosthesis, the actuator converts kinetic energy into first electrical energy that is greater than second electrical energy supplied to the actuator from the rechargeable battery. The prosthesis further includes a recharging circuit. The recharging circuit can receive at least a portion of the first electrical energy from the electric actuator and can supply some of the at least a portion of the first electrical energy to the rechargeable battery to recharge the rechargeable battery.

17 Claims, 7 Drawing Sheets

(51) Int. Cl.
*A61B 5/11* (2006.01)
*A61F 2/64* (2006.01)
*A61H 1/02* (2006.01)
*A61H 3/00* (2006.01)
*H02J 7/00* (2006.01)
*A61F 2/68* (2006.01)
*A61F 2/76* (2006.01)
*A61F 5/01* (2006.01)
*H02J 1/10* (2006.01)

(52) U.S. Cl.
CPC .............. *A61B 5/6828* (2013.01); *A61F 2/64* (2013.01); *A61H 1/0237* (2013.01); *A61H 3/00* (2013.01); *H02J 7/00304* (2020.01); *A61B 2562/0219* (2013.01); *A61F 2002/6818* (2013.01); *A61F 2002/701* (2013.01); *A61F 2002/702* (2013.01); *A61F 2002/704* (2013.01); *A61F 2002/708* (2013.01); *A61F 2002/768* (2013.01); *A61F 5/0123* (2013.01); *A61F 2005/0155* (2013.01); *A61H 2201/5061* (2013.01); *A61H 2201/5069* (2013.01); *A61H 2201/5084* (2013.01); *H02J 1/108* (2013.01); *H02J 7/00302* (2020.01); *H02J 7/00306* (2020.01); *H02J 7/0068* (2013.01); *H02J 7/007* (2013.01)

(56) References Cited

U.S. PATENT DOCUMENTS

| | | | |
|---|---|---|---|
| 2007/0233279 A1* | 10/2007 | Kazerooni | A61H 1/024 623/24 |
| 2008/0277943 A1* | 11/2008 | Donelan | F03G 5/00 290/1 R |
| 2010/0312363 A1 | 12/2010 | Herr et al. | |
| 2011/0144547 A1* | 6/2011 | Kusuura | A61H 1/0274 601/35 |
| 2013/0056981 A1* | 3/2013 | Mullins | F03G 5/00 290/7 |
| 2013/0317626 A1 | 11/2013 | Hasselgren et al. | |
| 2015/0075575 A1* | 3/2015 | Karlovich | A61H 3/008 135/66 |
| 2017/0196750 A1* | 7/2017 | Hepler | H02J 50/001 |

FOREIGN PATENT DOCUMENTS

| | | |
|---|---|---|
| WO | WO 2007/016781 | 2/2007 |
| WO | WO 2007-016781 A1 | 2/2007 |
| WO | WO 2007/025116 | 3/2007 |
| WO | WO 2007-025116 A2 | 3/2007 |
| WO | WO 2008/031220 | 3/2008 |
| WO | WO 2008-031220 A1 | 3/2008 |

OTHER PUBLICATIONS

International Search Report and Written Opinion dated Mar. 28, 2019 for International Application No. PCT/US2018/065018, 17 pages.

European Office Action issued in corresponding European Patent Application No. 18829681.8, dated Jul. 30, 2024, in 7 pages.

* cited by examiner

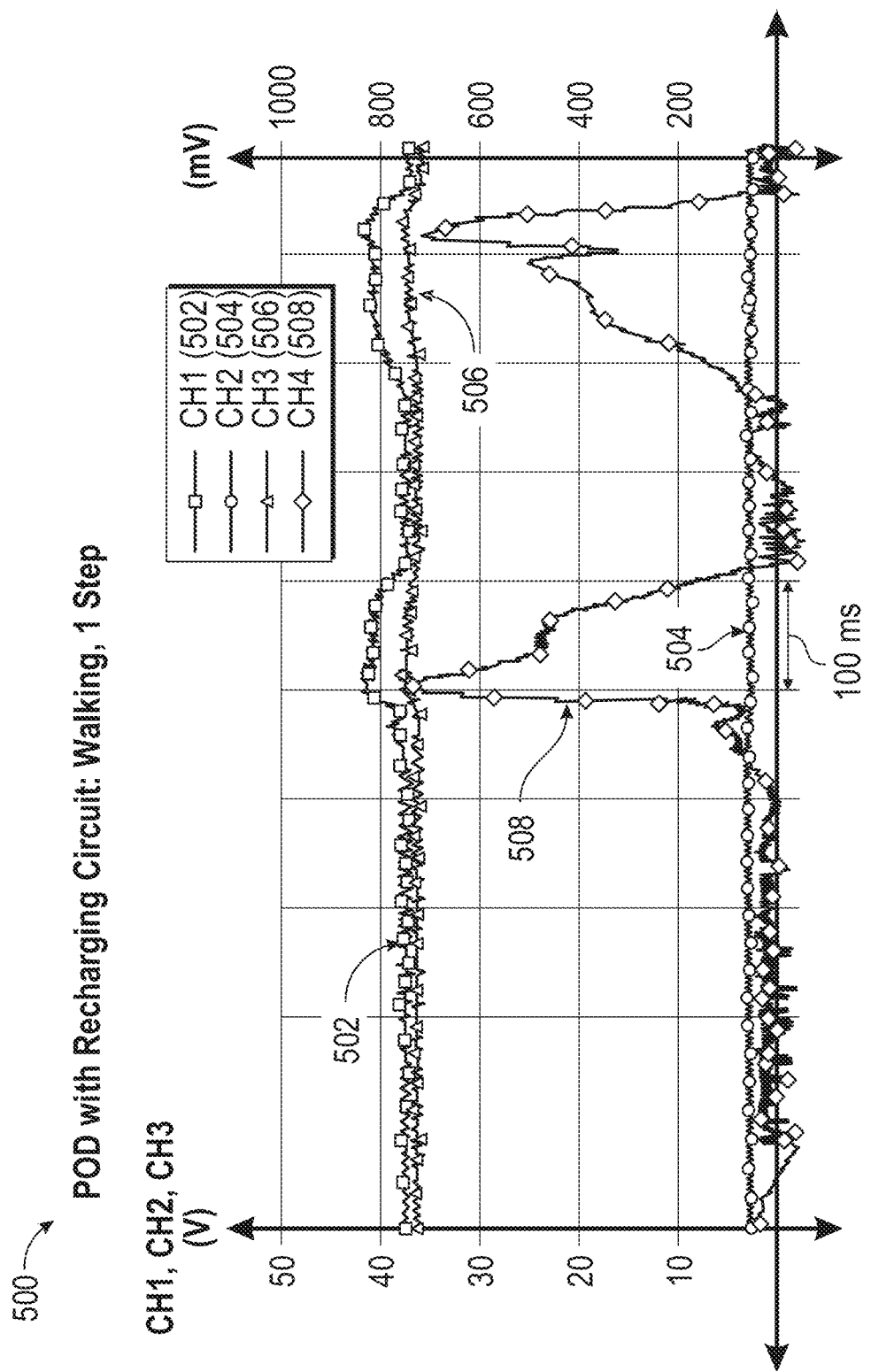

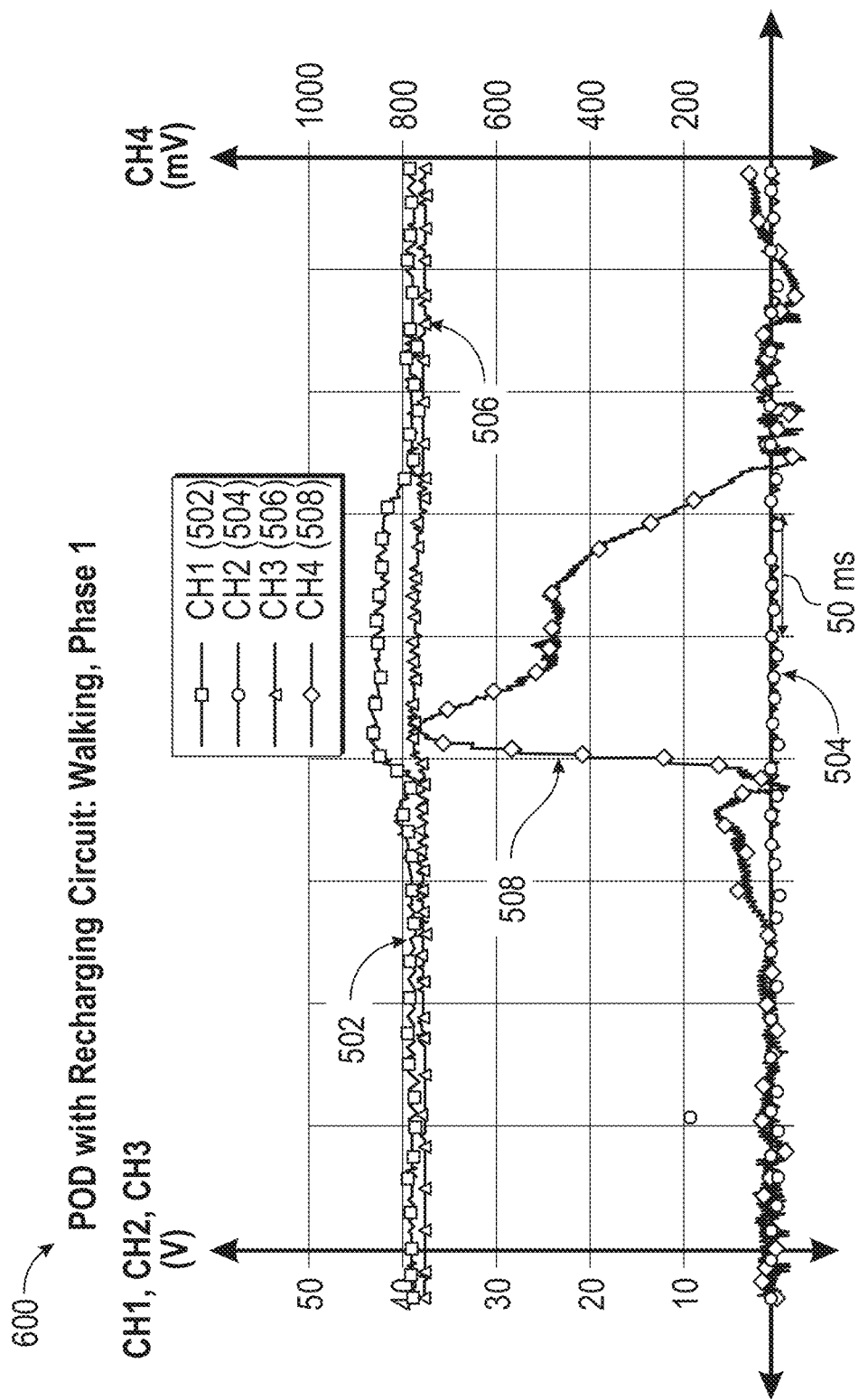

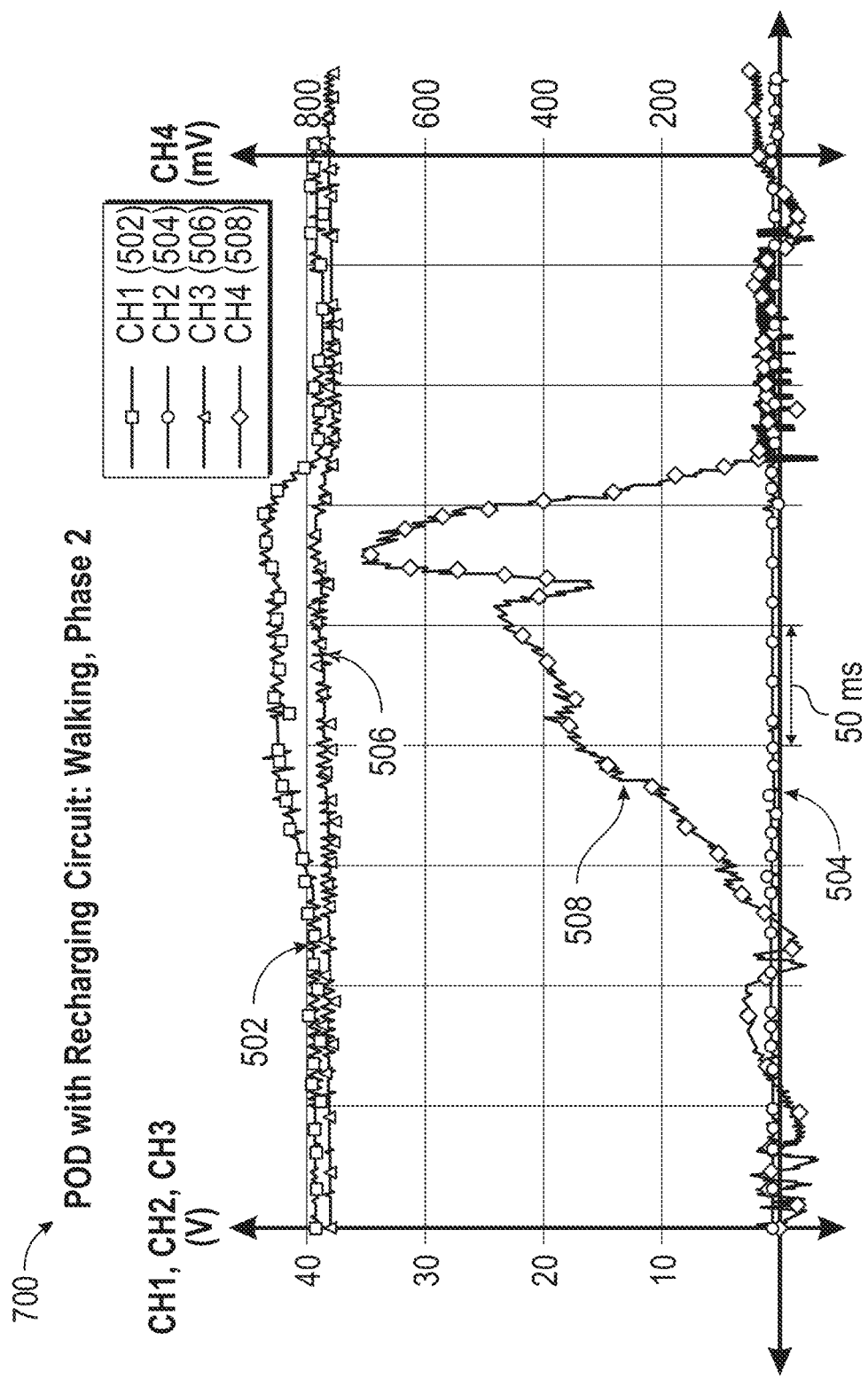

POWERED PROSTHETIC KNEE WITH BATTERY RECHARGING DURING REGENERATION PHASE

CROSS-REFERENCE TO RELATED APPLICATIONS

The present application claims priority benefit to U.S. Provisional App. No. 62/597,658, entitled "Powered Prosthetic Knee With Battery Recharging During Regeneration Phase," filed Dec. 12, 2017, which is hereby incorporated herein by reference in its entirety.

TECHNICAL FIELD

The present application generally relates to a powered prosthetic limb and more particularly to a powered prosthetic knee with regenerative braking.

BACKGROUND

Over the years, many kinds of prostheses have been devised in effort to replace the limbs that amputees have lost. In particular, efforts have been made to develop prostheses that will replace the loss of major limbs such as legs and arms in view of the immense impact that such a loss has on the amputee. All these prostheses have the difficult task of giving to these amputees as normal of a life as possible. The task is particularly difficult for leg prostheses due in part to the complexity of human locomotion.

To that end, battery powered electric motors or actuators have been incorporated into some prostheses to facilitate the amputee's gait cycle. However, power supplies are bulky or are incapable of powering a prosthesis for extended periods of time.

SUMMARY

The present disclosure describes example systems, methods, and apparatuses for increasing an energy efficiency of a prosthetic or orthotic device ("POD"). A POD can include a recharging circuit for recharging a battery of the POD during a portion of the amputee's gait cycle. At times when an actuator of the POD is generating (rather than consuming) electrical energy, the recharging circuit can receive electrical energy from the actuator and supply a controlled amount of electrical energy to the battery so the battery can recharge. The POD can include a prosthetic knee.

The POD of the preceding paragraph may also include any combination of the following features described in this paragraph, among others described herein. A POD can include a first limb member, a second limb member, a rechargeable battery, an electric actuator, and a recharging circuit. The electric actuator can be coupled to the first limb member and the second limb member to form a joint. The electric actuator can be electrically coupled to the rechargeable battery. The electric actuator can use energy received from the rechargeable battery to actuate the first limb member relative to the second limb member. During at least a portion of a gait cycle, the electric actuator can convert kinetic energy into first electrical energy that is greater than second electrical energy supplied to the electric actuator from the rechargeable battery. The recharging circuit can be electrically coupled to the electric actuator. The recharging circuit can be configured to receive at least a portion of the first electrical energy from the electric actuator and supply some of the first electrical energy to the rechargeable battery to recharge the rechargeable battery.

The POD of any of the preceding paragraphs may also include any combination of the following features described in this paragraph, among others described herein. The POD can be a powered prosthetic knee. The recharging circuit can include a voltage converter that down-converts a voltage of the at least a portion of the first electrical energy supplied to the rechargeable battery. The voltage converter can be a buck converter. The recharging circuit can include a current limiter that limits an amount of current supplied to the rechargeable battery. The amount of current supplied to the rechargeable battery can be based on charging requirements of the rechargeable battery. The recharging circuit can include a voltage limiter that limits an amount of voltage supplied to the rechargeable battery. The recharging circuit can include a diode that prohibits current from to the recharging circuit from the rechargeable battery.

The POD of any of the preceding paragraphs may also include any combination of the following features described in this paragraph, among others described herein. The POD can include enable/disable circuit configured to enable or disable the recharging circuit. The enable/disable circuit can include an electrical or mechanical switch. The POD can include reverse and/or in-rush current protection between the rechargeable battery and the electric actuator. The reverse and/or in-rush current protection can be configured to protect the battery from first electrical energy. The reverse and/or in-rush current protection can include a diode oriented to prevent reverse currents from reaching the rechargeable battery. The POD can include a capacitor electrically coupled in parallel to the electric actuator. The capacitor can include one or more of a super capacitor, a hybrid super capacitor, a ceramic capacitor, or an electrolytic capacitor.

The POD of any of the preceding paragraphs may also include any combination of the following features described in this paragraph, among others described herein. The POD can include a power dissipation circuit configured to dissipate at least some of the first electrical energy. The power dissipation circuit can include a brake chopper, a switch, and a resistor. The brake chopper can be configured to control the switch to allow at least some of the first energy to dissipate across the resistor. The rechargeable battery can be a lithium-based battery.

The POD of any of the preceding paragraphs may also include any combination of the following features described in this paragraph, among others described herein. The at least a portion of the gait cycle can include at least a portion of Stance phase. The at least a portion of the gait cycle can include at least a portion of Swing phase. The at least a portion of the gait cycle can correspond to Initial swing. The at least a portion of the gait cycle can correspond to Terminal swing. The at least a portion of the gait cycle can correspond to maximum flexion of the POD. The at least a portion of the gait cycle can correspond to maximum extension of the POD.

The POD of any of the preceding paragraphs may also include any combination of the following features described in this paragraph, among others described herein. The first electrical energy can correspond to counter electromotive force (EMF) induced by the electric actuator. The second electrical energy can correspond to a voltage of the rechargeable battery. The first electrical energy can correspond to a voltage induced by the electric actuator.

A POD, a regenerative power system, or a recharging circuit having one or more of the features described in the following description. A method of performing any of the preceding paragraphs or the following description.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 5 illustrates a graph representing various example voltages measured in the regenerative power system of FIG. 3B as a wearer of a POD walks about one step;

FIG. 6 illustrates a scaled view of the graph of FIG. 5; and

FIG. 7 illustrates a scaled view of the graph of FIG. 5.

DETAILED DESCRIPTION

Figure 1:
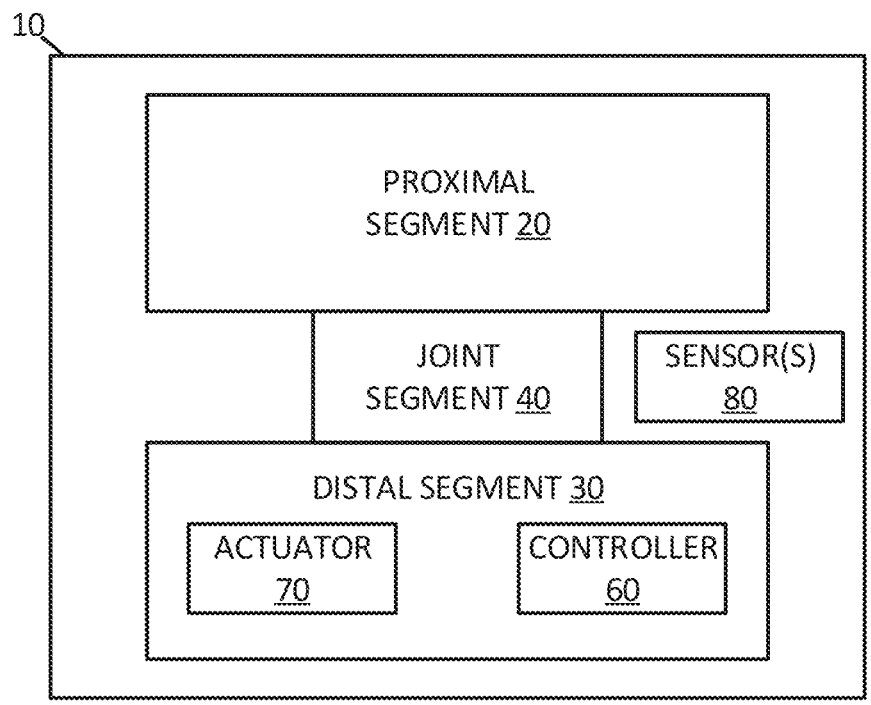
FIG. 1 is a block diagram of a prosthetic and/or orthotic device ("POD")

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

The present disclosure provides various examples of devices, systems and methods for harvesting energy supplied by an actuator of a POD during a regeneration phase and utilizing at least some of the energy to recharge the battery of the POD. A POD, such as a prosthetic knee, can include an actuator. The actuator can be a reversible machine in that it can function as a motor or a generator. For example, the actuator can function as a motor or a load when it receives energy from a battery and uses the energy to facilitate flexion and/or extension of one or more prosthetic limbs. The time at which the actuator functions as a motor can be referred to as a non-regeneration phase. In contrast, as another example, the actuator can function as a generator or brake when its rotational speed exceeds an amount of energy supplied by the battery, causing the actuator to develop a counter torque that acts as a brake. The time at which the actuator functions as a generator can be referred to as a regeneration phase. During a regeneration phase, the actuator converts its kinetic energy into electrical energy and supplies its electrical energy into the POD.

The electrical energy that is absorbed during a regeneration phase can be damaging to a POD, for example, causing overvoltage or overcurrent conditions. Consequently, to protect the battery and other components of the POD, many PODs dissipate this electrical energy as heat. However, the criticality of extending the battery life of the POD (thereby allowing amputees to retain as normal of a life as possible) gives merit to systems, methods, and devices that can recover and reuse this electrical energy, rather than merely wasting it in the form of heat dissipation. Accordingly, a recharging circuit as disclosed herein can be implemented into the POD to receive at least a portion of the electrical energy and supply it to the rechargeable battery, thereby recharging the battery and extending battery life. Although some PODs can store small amounts of the electrical energy for a short period of time in a storage element, such as a capacitor, the systems, methods, and devices described herein can allow for greater energy efficiency by recharging the battery.

Non-Limiting Examples

Walking is generally the most common activity of amputees who utilize a prosthetic knee. As a non-limiting example, a powered prosthetic knee can include a battery having a capacity of approximately 100 Watt-hours (or 360,000 Joules). In some cases, if the amputee walks at a pace of 4.0 km/hour, the prosthetic knee consumes approximately 42 Joules per step. It follows that, at 2000 steps per day, the prosthetic knee consumes about 84,000 Joules (or about 23.3% of the total energy in the battery), and at 4000 steps per day the prosthetic knee consumes about 168,000 Joules (or about 46.7% of the total energy in the battery).

As described herein, during portions of gait (non-limiting examples: Initial swing, Terminal swing, etc.), the actuator of the prosthetic knee undergoes various regeneration phases (also referred to as regenerative braking phases), which effectively cause the actuator to brake or decelerate movement of the prosthetic knee. During the various regeneration phases, rather than consuming energy, the actuator generates and supplies energy into the prosthetic knee. For example, if the wearer walks at a pace of 4.0 km/hour, the actuator can generate about 6.3 Joules per step during the various generation phases.

A prosthetic knee, as described herein, can include a recharging circuit coupled to the actuator. The recharging circuit can receive at least a portion of the energy generated by the actuator, and can supply the energy to the rechargeable battery to recharge the rechargeable battery, thereby increasing an energy efficiency of the prosthetic knee. As a non-limiting example, at 2000 steps per day, the recharging circuit can recover (e.g., supply to the battery) about 17,360 Joules (or about 4.8% of the total battery capacity). Similarly, at 4000 steps per day, the recharging circuit can recover about 34,720 Joules (or about 9.6% of the total battery capacity).

These examples are not intended to be limiting and disclose simply some of many possible embodiments. For example, PODs can have different battery capacities and/or can consume more or less energy per step, which can affect an amount of energy the recharging circuit can recover. Furthermore, similar regenerative braking techniques can be utilized in other PODs, such as a prosthetic knee, hip, shoulder, wrist, elbow, hand, digit, leg, ankle, foot, or the like.

Prosthetic or Orthotic Device

FIG. 1 illustrates a block diagram of a prosthetic and/or orthotic device ("POD") 10 having a regenerative and electronically controlled prosthetic joint. The POD 10 includes a proximal segment 20, a distal segment 30, a joint segment 40, an actuator 70, and a controller 60. The proximal segment 20 can include a socket to hold the stump of an above-knee or below-knee amputee. Furthermore, the proximal segment 20 can be connected to the distal segment 30 via the joint segment 40. The joint segment can be a knee joint, an ankle joint, or hip joint. In some embodiments, the POD 10 can include both a knee joint and an ankle joint. In some embodiments, the proximal segment 20 or the distal segment 30 includes the actuator 70. In other embodiments, the actuator 70 can be located between the proximal segment 20 and the distal segment 30. The actuator 70 can be implemented using a rotary actuator; however, other types of actuators may be used without departing from the spirit and scope of the description. The controller 60 can be located in any number of locations, including in or around the proximal segment 20, the distal segment 30, or the joint segment 40.

The POD 10 can include one of various prostheses. For example, the POD 10 can include a prosthetic knee, such as a prosthetic knee disclosed in U.S. patent application Ser. No. 12/160,727, filed Jul. 7, 2009, entitled "Joint Actuation Mechanism For A Prosthetic And/or Orthotic Device Having A Compliant Transmission" or U.S. patent application Ser. No. 12/523,710, filed Feb. 2, 2011, entitled "Reactive Layer Control System For Prosthetic And Orthotic Devices," each of which is hereby incorporated by reference in its entirety. As another example, the POD 10 can include a prosthetic hip, such as a prosthetic hip disclosed in U.S. patent application Ser. No. 13/837,124, filed Mar. 15, 2013, entitled "Powered Prosthetic Hip Joint," which is hereby incorporated by reference in its entirety. As another example, the POD 10 can include a prosthetic hand or elbow, such as a prosthetic hand or elbow disclosed in U.S. patent application Ser. No. 14/614,231, filed Feb. 4, 2015, entitled "Modular And Lightweight Myoelectric Prosthesis Components And Related Methods," which is hereby incorporated by reference in its entirety. As another example, the POD 10 can include a prosthetic hand, digit, or thumb, such as a prosthetic hand, digit, or thumb disclosed in U.S. patent application Ser. No. 13/580,303, filed Oct. 31, 2012, entitled "Hand Prosthesis" or U.S. patent application Ser. No. 12/085,608, filed Oct. 16, 2009, entitled "Prostheses With Mechanically Operable Digit Members," each of which is hereby incorporated by reference in its entirety. For example, in some cases, the distal segment 30 can be a shank portion or a foot portion and the proximal segment 20 can be a thigh portion or a shank portion.

Recharging Circuit

Figure 2:
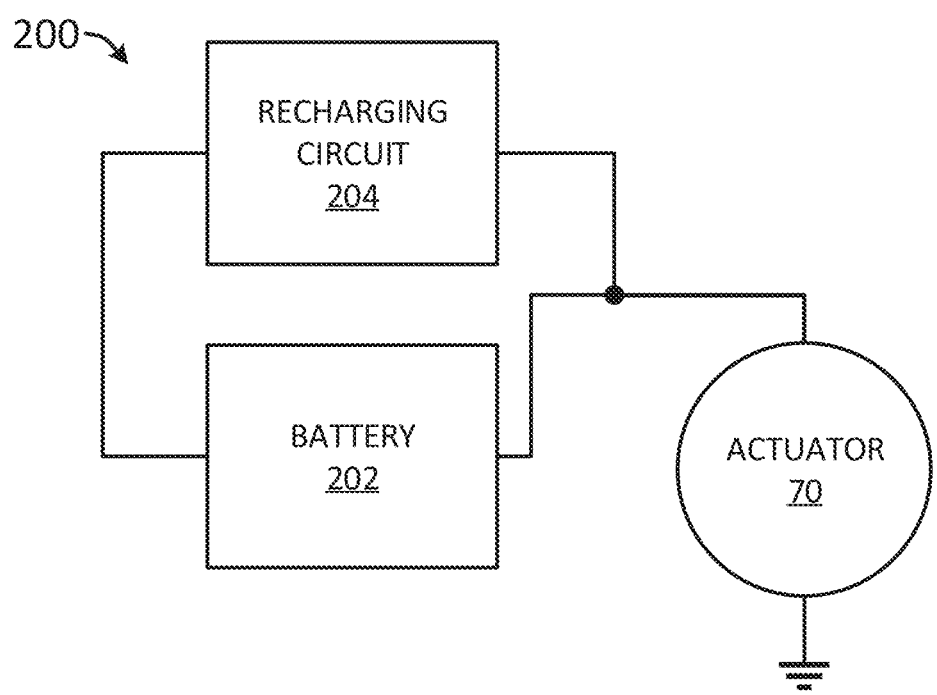
FIG. 2 is a diagram of an embodiment of a regenerative power system of a POD.

FIG. 2 illustrates a regenerative power system 200 of POD 10, according to some embodiments. The regenerative power system 200 includes the rechargeable battery 202, an actuator 70, and a recharging circuit 204. As described herein, the recharging circuit 204 can receive energy generated by the actuator 70 and can supply at least a portion of the energy generated by the actuator 70 to the rechargeable battery 202 to charge the rechargeable battery 202. Regenerative power system 200 advantageously increases energy efficiency over other PODs that dissipate or otherwise waste the energy generated by the actuator.

The rechargeable battery 202 is electrically coupled and supplies power to the actuator 70. The actuator 70 uses the energy supplied by the battery 202 to actuate a first limb member (e.g., distal segment 30) relative to a second limb member (e.g., proximal segment 20). Battery specifications may vary across embodiments. For example, a battery may be selected which fulfills power supply requirements of the actuator 70 or the regenerative power system 200, such as to deliver power to the actuator 70 within an operating range of the actuator 70.

In some cases, the battery 202 includes one or more battery cells arranged in series or parallel. For example, the battery 202 may include multiple battery cells, such as 2, 4, 6, 8, 10, 12, or 14 cells. The cells may be high-energy density cells, such as Lithium-ion (Li-ion), Lithium Polymer (Li-Pol), or the like. For example, the battery 202 may include, but is not limited to, a modified ten-cell rechargeable battery pack type 10S1P UR18650NSX.

An arrangement of the battery cells may vary an available voltage or current of the battery 202. For example, battery cells of the battery 202 can be serially arranged to allow for a relatively high current or can be arranged in parallel to allow for a relatively high voltage. As a non-limiting example, a battery may have 10 cells, each cell of the having a nominal voltage of about 3.6V and a fully charged voltage of about 4.2V. The cells may be serially arranged such that the battery 202 has a nominal voltage of approximately 36V and a maximum voltage of approximately 42V, when fully charged. These examples are not intended to be limiting. As described herein, the battery 202 can be appropriately sized or rated based on power supply requirements of the system 200.

The actuator 70 is electrically coupled to and can receive energy from the rechargeable battery 202. The actuator 70 uses or consumes energy from the battery 202 to actuate the prosthetic joint, thereby aiding wearer movement, such as standing up, sitting down, raising a leg, walking (e.g., knee extension or flexion), etc. For example, the actuator 70 can be coupled to a first limb member (such as distal segment 30) and a second limb member (such as proximal segment 20) to form a joint, and the actuator 70 can use energy received from the battery 202 to actuate the first limb member relative to the second limb member, or vice versa. Depending on the configuration of the actuator 70, it can facilitate different types of movement, such as flexion or extension.

In some embodiments, the actuator 70 is a four-quadrant device and is capable of functioning as a motor or functioning as a generator. During a non-generation phase (i.e., a time at which the actuator 70 is functioning as a motor), the actuator 70 converts energy from the battery 202 into torque to move to control the first limb member or the second limb member relative to the other limb member. During a regeneration phase (i.e., a time at which the actuator 70 is functioning as a generator), the actuator 70 can supply energy to the recharging circuit 204 or battery 202, rather than consume energy from the battery 202.

A regeneration phase can occur when the actuator 70 converts kinetic energy of the actuator into a back electromotive force (EMF) (also called counter EMF) that exceeds a voltage supplied to the actuator 70. Back EMF is an electromotive force or voltage and opposes the voltage and current that is supplied to the actuator 70, such as by the battery 202. As the electrical energy (e.g., back EMF) supplied by the actuator exceeds the electrical energy (e.g., battery voltage) supplied to the actuator 70, a regeneration phase begins. During a regeneration phase, the actuator 70 inverts the current direction and supplies at least some energy into the POD 10, rather than consuming energy from the battery 202.

A regeneration phase may occur during the various phases of gait. A single gait cycle is also known as a stride. Each gait cycle or stride can have two phases: Stance Phase, the phase during which the foot remains in contact with the ground; and Swing Phase, the phase during which the foot is not in contact with the ground. While a regeneration phase may occur during either Stance Phase or Swing Phase, a regeneration phase can most commonly occur during Swing Phase. During Swing Phase, the wearer lifts (e.g., including knee flexion) and swings (including knee extension) the limb to complete the stride length.

Four gait phases are involved in Swing Phase: 1) Pre-swing (end of Stance Phase), 2) Initial swing, 3) Mid swing, and 4) Terminal swing. During Pre-swing, the limb responds to an initial weight transfer with increased knee flexion. A regeneration phase can occur during Pre-swing, for example, if the wearer is falling and the knee is yielding under load. During Initial swing, the increased knee flexion lifts the foot for toe clearance, and hip flexion advances the limb. A regeneration phase can occur during Initial swing, such as near or at the end of knee flexion, which may correspond to maximum heel rise. During Mid swing, the knee is allowed to extend and swing forward. The phase ends when the swinging limb is forward and the tibia is vertical (e.g., hip and knee flexion postures are equal). During Terminal swing, limb advancement is completed by knee extension and ends when the foot strikes the floor. A regeneration phase may occur during Terminal swing, such as near or at the end of knee extension.

During a regeneration phase, which is sometimes referred to as regenerative braking, the actuator 70 develops a counter torque and causes the actuator to slow or brake, thereby decelerating an extension or flexion of a prosthetic limb. An intensity of a regeneration phase (e.g., an amount of energy generated by the actuator 70) or a frequency of regeneration phases that occur during gait may vary based on various factors, such as the wearer's cadence. For example, a faster gait speed may result in increased energy generated by the actuator 70, as well as a shorter duration and higher frequency of the regeneration phases.

As discussed above, an effect of a regeneration phase by the actuator 70 is an energy return on the elements of the regenerative power system 200, which could be damaging to elements such as the battery 202. In some cases, a power dissipation circuit can be utilized to lessen an effect of a regeneration phase by dissipating the excess energy. However, while dissipating the energy may prevent damage to the elements of the regenerative power system 200, a power dissipation circuit effectively wastes the energy generated by the actuator 70.

Real-Time or Predicted Gait Phase

In some embodiments, the controller 60, such a processing device of the controller 60, can identify a real-time gait phase of the wearer of the POD 10. For example, the controller 60 can be in communications with and receive sensor data from the sensor(s) 80. Based at least in part on the sensor data, the controller 60 can determine the real-time gait phase of the wearer of the POD 10. In some embodiments, the controller 60 can predict the gait phase of the wearer of the POD 10. For example, based at least in part on the wearer's pace or cadence, the controller 60 can predict when a particular gait phase of the wearer of the POD 10 will occur.

The sensor(s) 80 can capture information relating to load distribution, angles, orientation, position, movement or other data of the POD 10. This information may be processed in real-time and communicated to the controller 60. The sensor(s) 60 can include one or more sensors including, but not limited to, a force sensor, an acceleration or orientation sensor (for example, an accelerometer, a gyroscope, an orientation sensor, or a gravity sensor), an angle sensor, and/or one or more other sensors. In some embodiments, the sensor(s) can include one or more current, voltage, or torque sensors, which can be utilized to determine one or more currents, voltages, or torques in the POD 10, such as in a regenerative power system of the POD 10.

A force sensor can provide force measurement data corresponding to an amount of load applied to the POD 10 by the wearer. For example, the force sensor can be configured to measure a component of force applied to the POD 10 from the ground or other supporting surface in a direction substantially along or parallel to a shin longitudinal axis. In some cases, the force sensor can be implemented as a load cell.

Force measurement data from the force sensor can be used to determine various gait parameters associated with an interaction between the wearer and the POD. In some cases, the force sensor can include multiple force sensors, from which information regarding how the wearer distributes load across the POD 10 can be determined. For example, using force measurement data from a front force sensor configured to measure load on the front or toe end of the POD 10 and from a back force sensor configured to measure load on the rear or heel end of the POD 10, the controller 60 (or POD 10) can determine the wearer's front/back load distribution. That is, a higher toe end load (as compared to the heel end load) can indicate that the wearer is leaning forward on his toes, while a higher heel end load (as compared to the toe end load) can indicate that the wearer is leaning backward on his heels. Similar determinations can be made if the force sensor includes a right force sensor configured to measure load on the right side of the POD 10 and a left force sensor configured to measure load on the left side of the POD 10. That is, a higher right side load (as compared to the left side load) can indicate that the wearer is leaning to the right, while a higher left side load (as compared to the right side load) can indicate that the POD 10 is leaning to the left. In some cases, the system 100 can include any combination of one or more of a left side force sensor, a right side force sensor, a heel force sensor, a toe force sensor, or various other force sensors configured to measure at various locations of the POD 10.

An acceleration or orientation sensor can provide acceleration data corresponding to acceleration of the POD 10 in one or more axes. For example, an acceleration or orientation sensor can be configured to measure acceleration of the POD in multiple axes, such as two or three substantially mutually perpendicular axes. In addition or alternatively, an acceleration or orientation sensor can be configured to measure an orientation of at least one of the proximal segment 20 or the distal segment 30. In some cases, an acceleration or orientation sensor can be implemented as an accelerometer. In addition or alternatively, the sensor(s) 60 may include one or more other types of sensors in combination with, or in place of, accelerometers. For example, the sensor(s) 60 may include a gyroscope configured to measure the angular speed of body segments and/or the POD 10, an orientation sensor, or a gravity sensor.

The acceleration or orientation data from the acceleration or orientation sensor can be used to determine various gait phases or gait parameters. For example, using the acceleration or orientation data, the controller 60 can determine a shank angle, which can be described as an angle of the line of the shank (for example, corresponding to a shin of the wearer) relative to a line of the foot of the POD 10 or a walking surface. Using the acceleration or orientation data (together with or separately from other sensor data), the controller 60 can determine to what degree (if at all) the POD 10 is leaning in any direction, such as left, right, front, back, etc.

An angle sensor can provide angle measurement data corresponding an angle between the proximal segment 20 and the distal segment 30. As a non-limiting example, the POD 10 can be a prosthetic knee. The proximal segment 20 can extend from the wearer's thigh, the distal segment can correspond to the wearer's shank or shin, and the angle sensor can be configured to detect or measure a knee rotation angle (sometimes referred to as the knee angle or the joint angle). Using angle measurement data from the angle sensor, the controller 60 can determine the joint angle, and thus a degree to which the joint segment 40 is flexed or extended. For example, a 180 degree knee rotation angle can indicate that the POD 10 is straight (for example, the wearer's thigh and shank are parallel), while a 90 degree knee rotation angle can indicate that the POD is bent such that the wearer's shank is angled at 90 degrees relative to the wearer's thigh. Accordingly, the angle measurement data from the angle sensor can be used determine whether the POD 10 is angled, and, in some cases, the degree to which the POD 10 is angled.

Using the sensor data, such as any of the force measurement data, the acceleration or orientation data, the angle measurement data or other sensor data, the controller 60 can determine whether the POD 10 is on or off the ground or other supporting surface. In some cases, using the sensor data, the controller 60 can identify one or more of a heel strike, toe down, heel off, initial push off, toe off, start of a forward swing, mid forward swing, end of forward swing and/or heel strike preparation. Using the sensor data, the controller 60 can identify in real time, or predict, the occurrence of a particular gait phase such as the occurrence of Stance phase or Swing phase, or even the occurrence of Pre-swing, Initial swing, Mid swing, or Terminal swing. In some embodiments, the controller 60 can electrically connect or disconnect the recharging circuit 204 from the actuator 70 based at least in part on the real-time occurrence, or predicted occurrence, of a particular gait phase, for example a gait phase that is associated with a regeneration phase of the actuator 70. Various other techniques for determining a gait phase or parameters related to gait phases can be utilized such as those described in U.S. Patent Publication No. 2006/0195197, entitled "Sensing Systems and Methods For Monitoring Gait Dynamics," filed Feb. 2, 2006, which is hereby incorporated by reference in its entirety.

Regenerative Power Systems

Figure 3A:
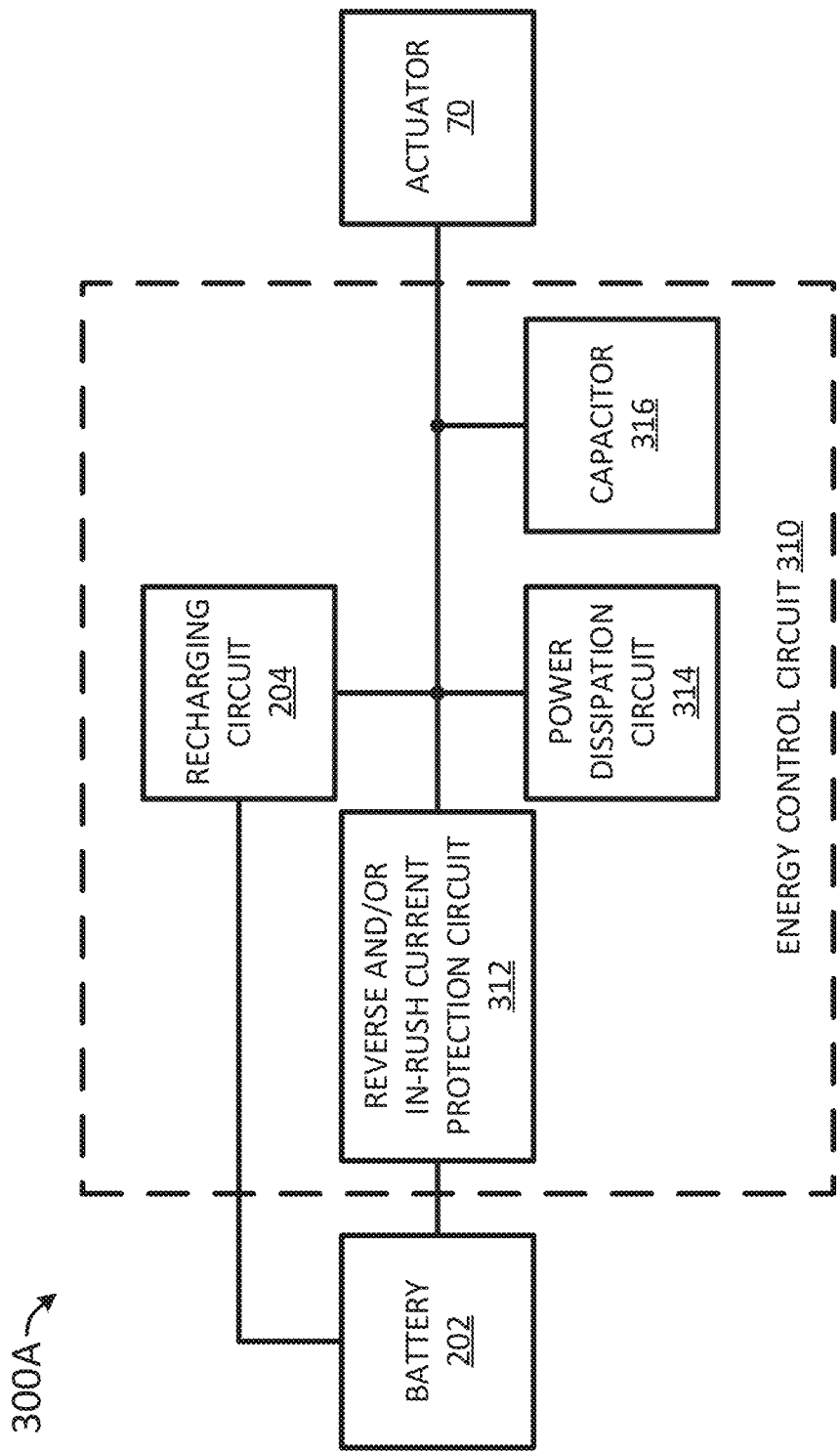
FIGS. 3A-3B are diagrams of a regenerative power system of a POD, according to some embodiments.
Figure 3B:
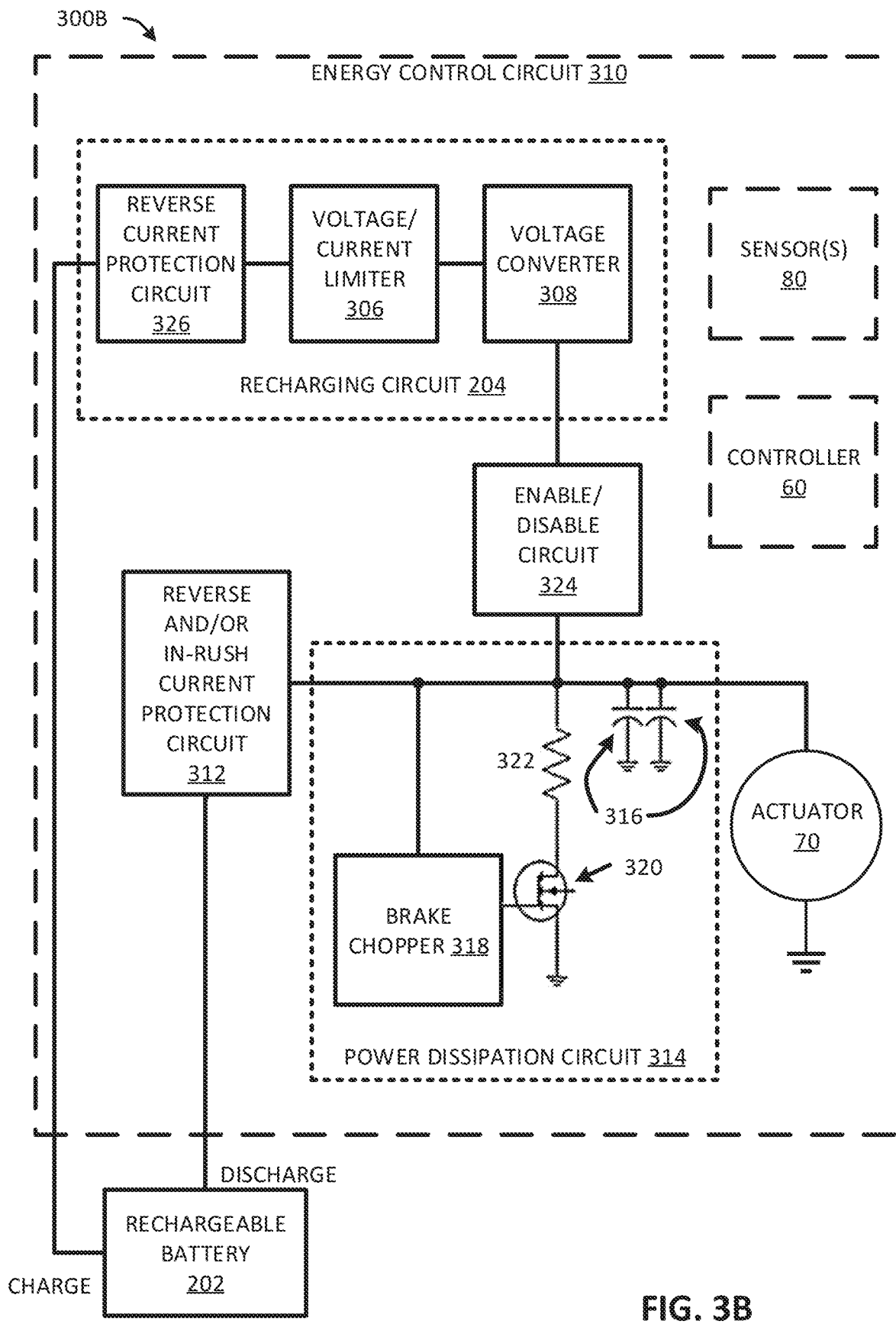

FIGS. 3A-3B illustrate regenerative power systems 300A and 300B of the POD 10, according to some embodiments. In the illustrated embodiment of FIGS. 3A and 3B, the regenerative power systems 300A and 300B include the battery 202, the actuator 70, the recharging circuit 204, as well as reverse and/or in-rush current protection circuit 312, one or more capacitors 316 or other type of short-term storage, and a power dissipation circuit 314. In some cases, the recharging circuit 204, the reverse and/or in-rush current protection circuit 312, the power dissipation circuit 314, and/or the capacitor 316 can collectively be referred to an energy control circuit 310. Furthermore, in some cases, the capacitor 316 can be part of the power dissipation circuit 314, as illustrated in FIG. 3B. In the illustrated embodiment of FIG. 3B, the regenerative power system 300B further includes enable/disable circuit 324 which can enable or disable (e.g., connect or disconnect) the recharging circuit 204. As described above with respect to FIGS. 1 and 2, the regenerative power systems 300A, 300B can be utilized in various PODs 10, including, but not limited to, a prosthetic knee, hip, shoulder, wrist, elbow, hand, digit, leg, ankle, foot, or the like.

During a regeneration phase of the actuator 70, electrical energy generated by the actuator 70 can be supplied to the energy control circuit 310. That is, the actuator 70 acts as a generator and supplies energy into the energy control circuit 310.

Although potentially useful for recharging the battery 202, the energy generated by the actuator 70 can damage one or more elements of the regenerative power system 300A, 300B if the energy from the actuator 70 is not properly controlled. In some cases, the energy control circuit 310 can protect the one or more elements of the regenerative power system 300A, 300B (such as the battery 202) from such energy. For example, in some embodiments, the energy control circuit 310 can include reverse and/or in-rush current protection circuit 312, which can protect the battery 202 from the energy generated by the actuator 70. The reverse and/or in-rush current protection circuit 312 can include a diode, such as an ideal diode, that prevents reverse currents from the actuator 70 from reaching the battery 202.

The reverse and/or in-rush current protection circuit 312 may protect the battery 202 during non-regeneration phases, as well. For example, the reverse and/or in-rush current protection circuit 312 can include an in-rush limiter that can be utilized to limit an amount of current drawn from the battery 202 by components of the regenerative power system 300A, 300B, such as capacitor 316. For example, when the regenerative power system 300A, 300B is powered off for a certain period of time, one or more capacitors 316 may become fully discharged. When the regenerative power system 300A, 300B is powered on, a high and fast power drain may be experienced by the battery 202 as the battery 202 charges the capacitor 316. This can result in a power drain that may exceed the maximum allowable power available. In order to protect the battery 202 from an over-discharge, a slow or fast in-rush limiter can limit, in time, the current drain of the capacitor 316 on the battery 202.

Power Dissipation Circuit

In certain embodiments, the battery/recharging protection circuit 310 can include a power dissipation circuit 314, which can dissipate at least some of the energy generated by the actuator 70 during a regeneration phase. In some cases, it may be advantageous for the power dissipation circuit 314 to dissipate energy received from the actuator 70. For example, if the battery 202 is fully or substantially charged, it may not be desirable to use the energy generated by the actuator 70 during a regeneration phase to charge the battery 202, as overcharging may damage the battery 202. In some embodiments, however, the battery 202 may be provided at less than full charge, such that any energy generated by the actuator 70 may be supplied to the battery 202.

The power dissipation circuit 314 can include various elements, which may be utilized to dissipate the energy supplied by the actuator 70. In some cases, the one or more capacitors 316 (e.g., one or more of an electrolytic capacitor, a super capacitor, a hybrid super capacitor, or a ceramic capacitor) can store at least some of the energy supplied by the actuator 70 during a regeneration phase. However, once the capacitors 316 have been fully charged, the system voltage (which can be measured over capacitors 316) may continue to increase to a level that could damage the regenerative power system 300A, 300B.

As illustrated in FIG. 3B, in some cases the power dissipation circuit 314 can include a brake chopper 318, an electrical or mechanical switch 320, a resistor 322, and/or one or more capacitors 316. During regeneration phases, the brake chopper 318 can limit or regulate the system voltage (e.g., the voltage at the actuator 70) by controlling the switch 320 to enable the resistor 322 such that energy is dissipated across the resistor 322 and converted to heat. In some cases, the brake chopper 224 or a controller 60 in communication with the brake chopper 224 can monitor a voltage (e.g., the system voltage), and the brake chopper 224 can control the switch 320 based on the monitored voltage. For example, if a monitored voltage satisfies a threshold voltage (non-limiting example: some voltage above the battery voltage), the brake chopper 224 can control the switch 320 to enable energy to be dissipated by the resistor 322. In some cases, if a monitored voltage does not satisfy a threshold voltage the brake chopper 224 can control the switch 320 (e.g., open the switch) to stop energy dissipation across the resistor 322.

Recharging Circuit

As described herein, the recharging circuit 204 is electrically coupled to the actuator 70 and is configured to receive at least a portion of the electrical energy from the actuator 70 and supply some of the electrical energy to the battery 202 to charge the battery 202. Particularly when the battery 202 is a Lithium battery, the battery 202 can be especially sensitive to charge current or voltage. For example, the integrity of the battery 202 could be damaged and/or the battery life shortened if the battery 202 is charged without proper control. Accordingly, the recharging circuit 204 can control the charging process such that the battery 202 is charged at an appropriate (e.g., safe, non-damaging, etc.) charge current and voltage. In some cases, the recharging circuit 204 can control one of the charge current or the charge voltage, without controlling the other.

The recharging circuit 204 can include a voltage converter 308, such as a buck converter, that down-converts voltage and up-converts current. In some cases, the output of the voltage converter 308 is a set voltage such as the battery voltage. Thus, when the voltage input of the voltage convertor, referred to as the system voltage, exceeds the battery voltage, the voltage converter 308 steps-down the system voltage so that the output of the voltage converter is approximately equivalent to the battery voltage. As the voltage converter steps-down the system voltage, the output current of the voltage convertor 308 can increase.

The recharging circuit 204 can include a current and/or a voltage limiter 306. The current limiter can limit an amount of current supplied by the recharging circuit 204 to the battery 202. As described herein, the battery 202 can be sensitive to charge current. For example, the integrity of the battery 202 could be damaged and/or the battery life shortened if the battery 202 is charged without proper control. Accordingly, the current limiter can ensure the current supplied to the battery 202 during charging corresponds to charging specifications of the battery 202. Similarly, the voltage limiter can limit an amount of voltage supplied by the recharging circuit 204 to the battery 202. As described herein, the battery 202 can be sensitive to charge voltage. Accordingly, the voltage limiter can ensure the voltage supplied to the battery 202 during charging corresponds to charging specifications of the battery 202.

The recharging circuit 204 can also include a reverse current protection circuit 326. For example, the reverse current protection circuit 326 can include a diode, such as an ideal diode, which can prevent current flow from the battery 202 to the recharging circuit 204, thereby protecting the recharging circuit 204. In some cases, rather than being included in the recharging circuit 204, the reverse current protection circuit 326 can be positioned between the battery 202 and the recharging circuit 204.

The regenerative power system 300A, 300B can include an enable/disable circuit 324 that can enable the recharging circuit 204 to charge the battery or prevent the recharging circuit 204 from charging the battery. For example, the enable/disable circuit 324 can include an electrical or mechanical switch, such as a field-effect transistor (FET), a metal-oxide-semiconductor FET (MOSFET), or a power FET, which can be configured in an open circuit configuration or a closed circuit configuration. Depending on its configuration, the recharging circuit 204 can be electrically connected or electrically disconnected from the actuator 70, the power dissipation circuit 314, or the rechargeable battery 202.

The enable/disable circuit 324 can, in some cases, be controlled based on one or more voltages or currents in the regenerative power system 300B. For instance, based on one or more sensed voltages, the enable/disable circuit 324 can create a closed circuit to enable the recharging circuit 204 to charge the battery or can create an open circuit, which can effectively disconnect the recharging circuit 204 from the actuator 70 and prevent the recharging circuit 204 from charging the battery. As a non-limiting example, if a sensed voltage, such as a battery voltage, does not satisfy a threshold voltage, the enable/disable circuit 324 can create an open circuit that disengages the recharging circuit 204 from the actuator 70 and/or prevents the recharging circuit 204 from charging the battery 202. As another example, if a sensed voltage does not satisfy a threshold voltage, the enable/disable circuit 324 can create a closed circuit to enable the recharging circuit 204 to charge the battery.

As described herein, the POD 10 can include a controller 60 and one or more sensors 80. In some embodiments, the controller 60 or the sensor(s) are part of the regenerative power system 300B. The controller 60 can be in communication with the control the enable/disable circuit 324, in some cases, can control the enable/disable circuit 324 based at least in part on data from the sensor(s) 80. For example, based on the sensor data from the sensor(s) 80, the controller 60 can control the enable/disable circuit 324 to either electrically connect or electrically disconnect the recharging circuit 204 from the actuator 70.

In some embodiments, the sensor data includes one or more voltages or currents of the regenerative power system 300B. For example, the sensor(s) 80 can be configured to measure one or more of a voltage or current of the rechargeable battery 202, a voltage or current drawn by the actuator 70, a voltage or current supplied by the actuator 70, a voltage or current of the recharging circuit 204, a voltage or current of the power dissipation circuit 314, or the like. Based at least in part on a determination that a particular one of the measured voltages or currents satisfies a first energy threshold, the controller 60 can cause the enable/disable circuit 324 to allow an electrical connection between the recharging circuit 204 and the actuator 70. As a non-limiting example, the first energy threshold can correspond to the voltage of the rechargeable battery 202. For example, the first energy threshold can be the voltage of the rechargeable battery 202 or can be the rechargeable battery 202 plus or minus some offset, such as a one or two percent or a few volts.

Continuing with the example, based on a determination that the voltage supplied by the actuator 70 satisfies the energy threshold, the controller 60 can cause the enable/disable circuit 324 to allow an electrical connection between the recharging circuit 204 and the actuator 70, which can allow the recharging circuit 204 to utilize the power generated by the actuator 70 to recharge the rechargeable battery 202. Similarly, based on a determination that the voltage supplied by the actuator 70 does not satisfy the energy threshold, the controller 60 can cause the enable/disable circuit 324 to disallow an electrical connection between the recharging circuit 204 and the actuator 70, which can effectively electrically disconnect the recharging circuit 204 from the actuator 70.

In some embodiments, the energy threshold does not correspond to the battery voltage. For example, the energy threshold can be a predetermined voltage, current, or power, or can be associated with one or more other components of the regenerative power system 300B, such as a current or voltage for which the actuator 70 is rated, or a current or voltage the actuator 70 is expected to draw during a non-regeneration phase.

In some embodiments, as described herein, the controller 60 can use the sensor data from the sensor(s) 80 to identify a gait phase of the wearer of the POD 10, such as a real-time gait phase or an expected or predicted gait phase. Based at least in part on the gait phase, the controller 60 can cause the enable/disable circuit 324 to allow or disallow an electrical connection between the recharging circuit 204 and the actuator 70. As an example, based at least in part on the sensor data from the sensor(s) 80, the controller 60 can determine that the wearer is performing an Initial swing. Based at least in part on the determination that the wearer is performing an Initial swing, the controller 60 can cause the enable/disable circuit 324 to allow an electrical connection between the recharging circuit 204 and the actuator 70. In some instances, the controller 60 can also determine that the wearer is near or at the end of knee flexion during the Initial swing. Based at least in part on the determination that the wearer is near or at the end of knee flexion during the Initial swing, the controller 60 can cause the enable/disable circuit 324 to allow an electrical connection between the recharging circuit 204 and the actuator 70. Similarly, based at least in part on the determination that the wearer is near or at the end of knee extension during the Terminal swing, the controller 60 can cause the enable/disable circuit 324 to allow an electrical connection between the recharging circuit 204 and the actuator 70. As another example, based at least in part on the sensor data from the sensor(s) 80, the controller 60 can determine that the wearer is performing a Mid swing. Based at least in part on the determination that the wearer is performing a Mid swing, the controller 60 can cause the enable/disable circuit 324 to disallow an electrical connection between the recharging circuit 204 and the actuator 70, for example, causing the enable/disable circuit 324 to become an open circuit.

In some embodiments, the controller 60 can control whether the enable/disable circuit 324 allows or disallows an electrical connection between the recharging circuit 204 and the actuator 70, based at least in part on an anticipated, expected, or predicted gait phase. For example, based at least in part on the sensor data from the sensor(s) 80, the controller 60 can determine a pace or cadence of the wearer of the POD 10, such as during ambulation. Based at least in part of the pace or cadence, the controller 60 can anticipate or predict a time at which a particular gait phase occurs (non-limiting examples: near or at the end of knee flexion during the Initial swing, near or at the end of knee extension during the Terminal swing), and can cause the enable/disable circuit 324 to allow (or disallow) an electrical connection between the recharging circuit 204 and the actuator 70 based at least in part on the predicted time of the particular gait phase. In some embodiments, the controller 60 or the enable/disable circuit 324 can include a comparator circuit, which can compare one or more of the measured voltages or currents to an energy threshold. Based on the output of the comparator circuit, the enable/disable circuit 324 can electrically connect or electrically disconnect the recharging circuit 204.

Although illustrated in FIG. 3B as being location or positioned between the recharging circuit 204 and the actuator 70, the enable/disable circuit 324 can be positioned at one or more additional or alternative locations in the regenerative power systems 300B. For example, in some embodiments, the enable/disable circuit 324 is positioned between the recharging circuit 204 and the rechargeable battery 202, and can electrically connect or electrically disconnect the recharging circuit 204 and the rechargeable battery 202.

POD with Power Dissipation Circuit

As described herein, powered prosthetic knees can facilitate ambulation. However, with some designs, a considerable amount of energy is lost or wasted by a power system of a powered prosthetic knee. For example, during a regeneration phase of an actuator, many power systems dissipate the energy generated by the actuator through a power dissipation circuit.

Figure 4:
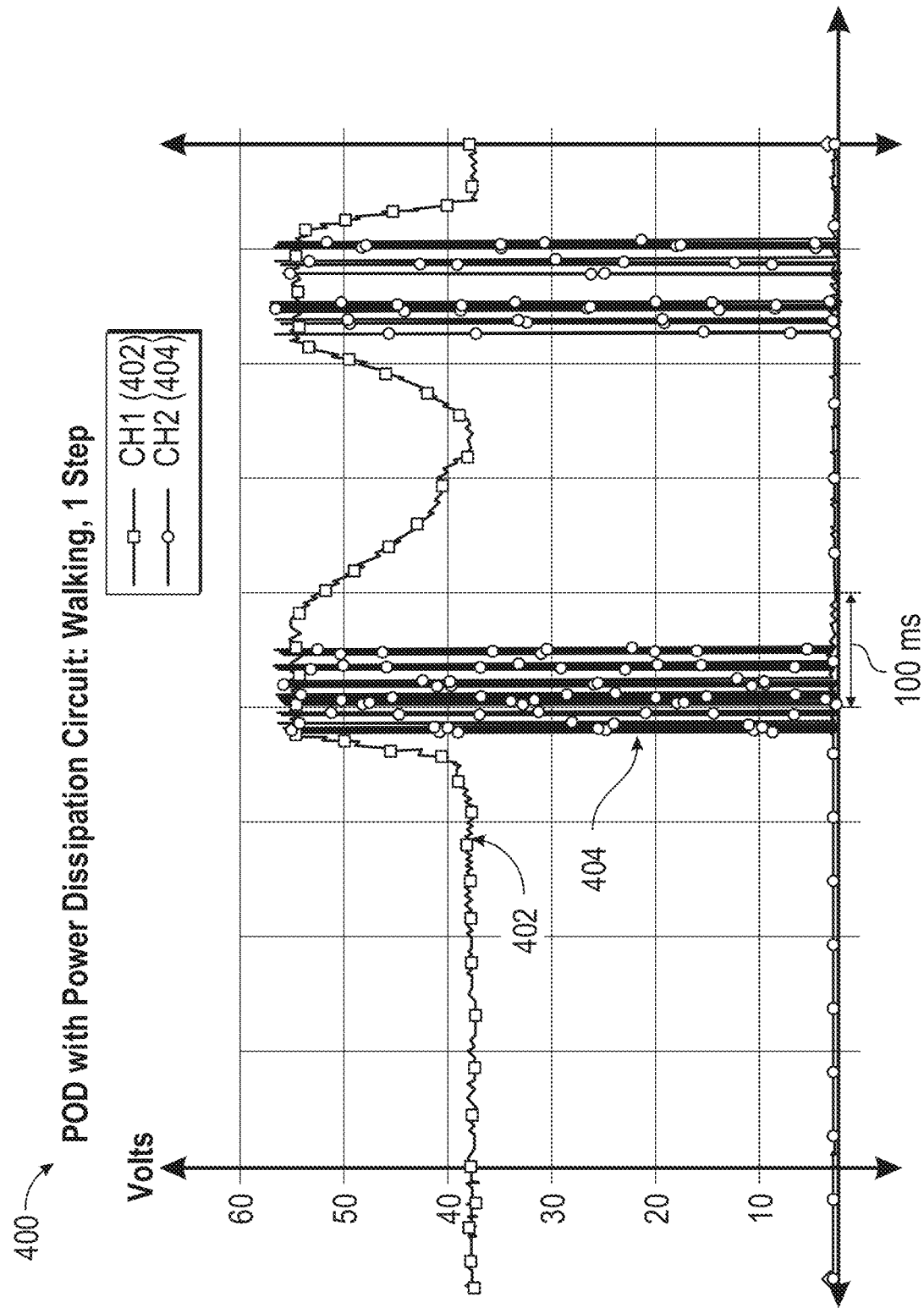
FIG. 4 illustrates a graph representing various voltages of a prosthetic knee configured to dissipate energy generated during a regeneration phase, according to some embodiments.

FIG. 4 illustrates a graph 400 representing various voltages of a prosthetic knee configured to dissipate energy generated during a regeneration phase, according to some embodiments. In this example, a wearer of the prosthetic knee walked about one step. As described above, in the illustrated embodiment, the power system includes a power dissipation circuit configured to dissipate energy generated by the actuator during a regeneration phase, and does not include a recharging circuit. The graph 400 illustrates two channels 402, 404. Channel 1 402 corresponds to a system voltage measured over a capacitor connected in parallel with an actuator. Channel 2 404 corresponds to a voltage measured over a resistor that is part of power dissipation circuit, and thus corresponds to an amount of power dissipated by the power system. The vertical axis (y-axis) corresponds to voltage and has a step size of a step size of 10 V. The horizontal axis (x-axis) corresponds to time and has a step size of 100 ms.

The graph 400 illustrates how the system voltage 402 and power dissipation circuit voltage 404 change over time as a wearer walks one step using the prosthetic knee. In this example, an envelope of Channel 1 402 and Channel 2 404 presents a pattern characterized by a relatively flat and constant portion, followed by a first maxima and a second maxima. The relatively flat and constant portion corresponds to Stance Phase, during which time no regeneration phases occur. The first maxima corresponds to maximum knee flexion (e.g., Initial swing) during Swing Phase, and represents a first regeneration phase of the actuator. The second maxima corresponds to maximum knee extension (e.g., Terminal swing) during Swing Phase, and represents a second regeneration phase of the actuator.

In the illustrated embodiment, during non-regeneration phases the system voltage 402 follows the battery voltage (e.g., approximately 36V). As the actuator enters the first regeneration phase and begins to supply energy into the system (e.g., corresponding to the first train of voltage pulses in Channel 2 404 and the first maxima of Channel 1 402), the system voltage 402 increases (e.g., to approximately 55V). To avoid damage to elements of the POD 10, a power dissipation circuit dissipates some of this energy introduced by the actuator. The energy dissipated is illustrated by the first train of voltage pulses in Channel 2 404. Similarly, as the actuator enters the second regeneration phase and begins to supply energy into the system (e.g., corresponding to the second train of voltage pulses in Channel 2 404 and the second maxima of Channel 1 402), the system voltage 402 increases (e.g., to approximately 55V). To avoid damage to elements of the POD 10, a power dissipation circuit dissipates some of this energy introduced by the actuator. The energy dissipated is illustrated by the second train of voltage pulses in Channel 2 404.

In this example, each pulse of the train of voltage pulses lasts for about 100 vs. In addition, there are approximately 90 pulses (about 45 pulses per generation phase). Accordingly, given that the power dissipation circuit dissipates the excess power over a 4.3-ohm resistor, the total power dissipated through the power dissipation circuit, per step, is approximately 6.33 Joules.

POD with Recharging Circuit

FIG. 5 illustrates a graph 500 representing various example voltages measured in regenerative power system 300B as an amputee walks about one step. As illustrated, the graph 500 includes four channels 502, 504, 506, 508. Channel 1 502 corresponds to a system voltage measured over a capacitor 316, which is connected in parallel with actuator 70. Channel 2 504 corresponds to a voltage measure over resistor 322 of the power dissipation circuit 314. Channel 3 506 corresponds to an output voltage of a voltage converter 308. Channel 4 508 corresponds to an output voltage of the recharging circuit 70.

The vertical axis corresponds to voltage, and the horizontal axis corresponds to time, in ms. As noted in FIG. 5, along the vertical axis, Channel 1 502, Channel 2 504, and Channel 3 506 have a step size of 10 V, and Channel 4 508 has a step size of 200 mV. The horizontal axis has a step size of 100 ms.

In this example, an envelope of Channel 1 502 and Channel 4 508 presents a pattern characterized by a relatively flat and constant portion, followed by a first maximum and a second maxima. The relatively flat and constant portion corresponds to Stance Phase, during which time no regeneration phases occur. The first maxima corresponds to maximum knee flexion (e.g., Initial swing) during Swing Phase, and represents a first regeneration phase of the actuator. The second maxima corresponds to maximum knee extension (e.g., Terminal swing) during Swing Phase, and represents a second regeneration phase of the actuator.

As illustrated, during non-regeneration phases the system voltage 502 and the output 506 of the voltage converter 308 follow the battery voltage (e.g., approximately 36V). As the actuator enters the first and second regeneration phases and begins to supply energy into the system (corresponding to the first and second maxima of Channel 1 502 and Channel 4 508), the system voltage 502 increases. As the system voltage 502 reaches a set point voltage (in this example, about 41.5V), the voltage converter 308 steps-down the output voltage 502 and steps-up the current output of the voltage converter 308. The recharging circuit 306 supplies power to the battery to recharge the battery until the regeneration phase ends, the recharging circuit supplies its power, or the regeneration circuit is disabled. During the first and second regeneration phases, the recharging circuit is able to provide the battery 202 a recharging power of about 8.68 Joules. In some cases, at least some of the energy (e.g., about 0.25 Joules) from the actuator 70 is stored in the capacitors 316.

FIG. 6 illustrates a scaled view of the first regeneration phase of the graph of FIG. 5, which corresponds to maximum knee flexion (e.g., Initial swing) during Swing Phase. As illustrated, prior to the regeneration phase, the system voltage 502 is approximately equal to the battery voltage. As the first regeneration phase occurs, the system voltage 502 increases and output voltage of the recharging circuit 508 correspondingly increases. In some embodiments, the recharging circuit 204 supplies the increased voltage to the battery 202 until the regeneration phase ends or until a non-regeneration phase begins. For example, as described herein, the recharging circuit 204 can be electrically disconnected from the actuator 70 responsive to a measured voltage or current failing to satisfy an energy threshold. Alternatively, in some cases, the recharging circuit 204 may require a certain amount of voltage or current to be activated or turned over. Accordingly, during a non-regeneration phase, the recharging circuit 204 may remain electrically connected to the actuator 70, yet it does not charge the rechargeable battery because the current or voltage provided to the recharging circuit 204 may not satisfy a "turn-on" voltage or current of the recharging circuit 204. During the first regeneration phase, the recharging circuit is able to supply approximately 4.18 Joules to the battery 202.

FIG. 7 illustrates a scaled view of the second regeneration phase of the graph of FIG. 5. As the second regeneration phase occurs, the system voltage 502 increases and output voltage of the recharging circuit 508 correspondingly increases. The recharging circuit 204 supplies the increased voltage to the battery 202 until the regeneration phase ends. During the second regeneration phase, the recharging circuit 204 is able to supply approximately 4.5 Joules to the battery 202.

As illustrated by FIGS. 5-7, energy coming from the actuator during a regeneration phase can be supplied to the battery 202, thereby increasing a system autonomy and increasing an overall efficiency of the regenerative power system.

Example Embodiments

Various example embodiments of apparatuses, methods, and systems relating to recharging a rechargeable battery of a prosthetic or orthotic device ("POD") can be found in the following clauses:

Clause 1. A prosthetic or orthotic device (POD) comprising:
  an electric actuator coupled to a first limb member and a second limb member to form a joint, and electrically coupled to a rechargeable battery;
  wherein the electric actuator uses energy received from the rechargeable battery to actuate the first limb member relative to the second limb member,
  wherein during at least a portion of a gait cycle, the electric actuator converts kinetic energy into first electrical energy that is greater than second electrical energy supplied to the electric actuator from the rechargeable battery; and
  a recharging circuit configured to:
    receive at least a portion of the first electrical energy from the electric actuator, and
    supply at least some of the at least a portion of the first electrical energy to the rechargeable battery to recharge the rechargeable battery.

Clause 2. The POD of Clause 1, further comprising the first limb member, the second limb member, or the rechargeable battery.

Clause 3. The POD of any one or more of the previous clauses, wherein the POD comprises a powered prosthetic knee.

Clause 4. The POD of any one or more of the previous clauses, wherein the at least a portion of the gait cycle comprises at least a portion of Swing phase of the gait cycle.

Clause 5. The POD of any one or more of the previous clauses, wherein the at least a portion of the gait cycle comprises at least a portion of at least one of Initial swing or a Terminal swing.

Clause 6. The POD of any one or more of the previous clauses, wherein the at least a portion of the gait cycle comprises at least a portion of at least two of Pre-swing, Initial swing phase, Mid swing, or Terminal swing.

Clause 7. The POD of any one or more of the previous clauses, wherein the at least a portion of the gait cycle comprises at least a portion of the gait cycle corresponding to a maximum extension of the POD or a maximum flexion of the POD.

Clause 8. The POD of any one or more of the previous clauses, wherein the first electrical energy corresponds to counter electromotive force (EMF) induced by the electric actuator.

Clause 9. The POD of any one or more of the previous clauses, wherein the second electrical energy corresponds to a voltage of the rechargeable battery.

Clause 10. The POD of any one or more of the previous clauses, wherein the recharging circuit is further configured to down-convert a voltage of the at least some of the at least a portion of the first electrical energy supplied to the rechargeable battery.

Clause 11. The POD of any one or more of the previous clauses, wherein the recharging circuit is further configured to control an amount of current or voltage supplied to the rechargeable battery.

Clause 12. The POD of any one or more of the previous clauses, further comprising an enable/disable circuit configured to provide an open or closed circuit between the actuator and the recharging circuit.

Clause 13. The POD of any one or more of the previous clauses, further comprising a power dissipation circuit configured to dissipate at least some of the first electrical energy.

Clause 14. The POD of Clause 13, wherein the power dissipation circuit comprises a brake chopper, a switch, and a resistor.

Clause 15. The POD of any of clauses 13 or 14, wherein the brake chopper is configured to control the switch to allow at least some of the first energy to dissipate across the resistor.

Clause 16. A regenerative power system for a prosthetic or orthotic device (POD), the system comprising:
a recharging circuit electrically coupled to a rechargeable battery and configured to be electrically coupled to an electric actuator that uses energy received from the rechargeable battery to actuate the first limb member relative to the second limb member, wherein during at least a portion of a gait cycle of a wearer of the powered prosthetic knee the electric actuator converts kinetic energy into first electrical energy that is greater than second electrical energy supplied to the electric actuator from the rechargeable battery, wherein the recharging circuit is configured to:
receive at least a portion of the first electrical energy from the electric actuator, and
supply at least some of the at least a portion of the first electrical energy to the rechargeable battery to recharge the rechargeable battery.

Clause 17. The system of Clause 16, wherein the at least a portion of the gait cycle comprises at least a portion of Swing phase of the gait cycle.

Clause 18. The system of any of Clauses 16 or 17, wherein the at least a portion of the gait cycle comprises at least a portion of at least one of Initial swing or Terminal swing.

Clause 19. The system of any of Clauses 16 to 18, wherein the at least a portion of the gait cycle comprises at least a portion of at least two of Pre-swing, Initial swing, Mid swing, or Terminal swing.

Clause 20. The system of any of Clauses 16 to 19, wherein the at least a portion of the gait cycle corresponds to a maximum extension of the POD.

Clause 21. The system of any of Clauses 16 to 20, wherein the at least a portion of the gait cycle corresponds to a maximum flexion of the POD.

Clause 22. The system of any of Clauses 16 to 21, wherein the first electrical energy corresponds to counter electromotive force (EMF) induced by the electric actuator, and wherein the second electrical energy corresponds to a voltage of the rechargeable battery.

Clause 23. The system of any of Clauses 16 to 22, wherein the recharging circuit is further configured to down-convert a voltage of the at least some of the at least a portion of the first electrical energy supplied to the rechargeable battery.

Clause 24. The system of any of Clauses 16 to 23, wherein the recharging circuit is further configured to control an amount of current or voltage supplied to the rechargeable battery.

Clause 25. The system of any of Clauses 16 to 24, further comprising an enable/disable circuit configured to provide an open or closed circuit between the actuator and the recharging circuit.

Clause 26. The system of any of Clauses 16 to 25, further comprising a power dissipation circuit configured to dissipate at least some of the first electrical energy.

Clause 27. The system of Clause 26, wherein the power dissipation circuit comprises a brake chopper, a switch, and a resistor.

Clause 28. The system of Clauses 26 or 27, wherein the brake chopper is configured to control the switch to allow at least some of the first energy to dissipate across the resistor.

Clause 29. The system of any of Clauses 16 to 28, wherein the POD comprises a powered prosthetic knee.

Clause 30. The system of any of the previous clauses, further comprising an enable/disable circuit configured to provide an open or closed circuit between the rechargeable battery and the recharging circuit.

Various example embodiments of apparatuses, methods, and systems relating to recharging a rechargeable battery of a prosthetic or orthotic device ("POD") can be found in the following clauses:

Clause 1. A prosthetic or orthotic device comprising:
an electric actuator coupled to a first limb member and a second limb member to form a joint, and electrically coupled to a rechargeable battery, wherein the electric actuator uses electrical energy received from the rechargeable battery to actuate the first limb member relative to the second limb member;
a recharging circuit; and
a controller configured to:
receive sensor data from one or more sensors,
identify a gait phase of a gait cycle of a wearer of the powered prosthetic knee based at least in part on the sensor data, and
based at least in part on the identification of the gait phase, cause the recharging circuit to receive second electrical energy from the electric actuator and supply at least some of the second electrical energy to the rechargeable battery to recharge the rechargeable battery.

Clause 2. The powered prosthetic knee of Clause 1, wherein the controller is further configured to, based at least in part on the identification of the gait phase, electrically connect to the electric actuator, wherein upon electrical connection the recharging circuit receives second electrical energy from the electric actuator and supplies at least some of the second electrical energy to the rechargeable battery to recharge the rechargeable battery Clause 3. The POD of any of the previous clauses, wherein the gait phase of the wearer of the powered prosthetic knee comprises a real-time gait phase of the wearer of the powered prosthetic knee.

Clause 4. The POD of any of the previous clauses, wherein the POD comprises a prosthetic knee.

Clause 5. The POD of any of the previous clauses, wherein the gait phase comprises at least a portion of a Swing phase of the gait cycle.

Clause 6. The POD of any of the previous clauses, wherein the gait phase comprises at least a portion of at least one of Initial swing of the gait cycle or Terminal swing of the gait cycle.

Clause 7. The POD of any of the previous clauses, wherein the gait phase comprises at least a portion of at least two of Pre-swing, Initial swing, Mid swing, or Terminal swing.

Clause 8. The POD of any of the previous clauses, wherein the gait phase of the gait cycle corresponds to a maximum extension of the POD during the gait cycle.

Clause 9. The POD of any of the previous clauses, wherein the gait phase of the gait cycle corresponds to a maximum flexion of the POD during the gait cycle.

Clause 10. The POD of any of the previous clauses, wherein the gait phase of the gait cycle corresponds to an end of knee flexion during Initial swing of the gait cycle.

Clause 11. The POD of any of the previous clauses, wherein the gait phase of the gait cycle corresponds to an end of knee extension during Terminal swing of the gait cycle.

Clause 12. The POD of any of the previous clauses, wherein during the gait phase, the electric actuator converts kinetic energy into the second electrical energy that is greater than the first electrical energy supplied to the electric actuator from the rechargeable battery.

Clause 13. The POD of any of the previous clauses, wherein the gait phase of the gait cycle is a first gait phase of the gait cycle, wherein the controller is further configured to:
identify a second gait phase of the gait cycle of the wearer of the powered prosthetic knee based at least in part on the sensor data, and
based at least in part on the identification of the second gait phase, cause the recharging circuit to electrically disconnect to the electric actuator.

Clause 14. The POD of Clause 13, wherein upon the electrical disconnection of the recharging circuit from the actuator, the recharging circuit does not receive electrical energy from the electric actuator.

Clause 15. The POD of any of Clauses 13 or 14, wherein upon the electrical disconnection of the recharging circuit from the actuator, the recharging circuit does not supply electrical energy to the rechargeable battery to recharge the rechargeable battery.

Clause 16. The POD of any of Clauses 13 to 15, wherein the second gait phase of the wearer of the powered prosthetic knee comprises a real-time gait phase of the wearer of the powered prosthetic knee.

Clause 17. The POD of any of Clauses 13 to 16, wherein the second gait phase comprises at least a portion of a stance phase of the gait cycle.

Clause 18. The POD of any of Clauses 13 to 17, wherein the second gait phase comprises at least a portion of the Swing phase of the gait cycle.

Clause 19. The POD of any of Clauses 13 to 18, wherein the second gait phase comprises at least a portion of at least two of Pre-swing, Initial swing, Mid swing, or Terminal swing.

Clause 20. The POD of any of Clauses 13 to 19, wherein the second gait phase comprises at least a portion of at least one of Initial swing of the gait cycle or Terminal swing of the gait cycle.

Clause 21. The POD of any of Clauses 13 to 20, wherein the second gait phase comprises all portions of the gait cycle other than the first gait phase.

Clause 22. The POD of any of Clauses 13 to 21, wherein during the second gait phase, the electric actuator consumes energy from the rechargeable battery.

Clause 23. A method of charging a rechargeable battery of a powered prosthetic knee, the method comprising:
receiving sensor data from one or more sensors of the powered prosthetic knee, wherein the powered prosthetic knee comprises a first limb member, a second limb member, a rechargeable battery, an electric actuator, and a recharging circuit, wherein the electric actuator is coupled to the first limb member and the second limb member to form a joint, wherein the electric actuator uses energy received from the rechargeable battery to actuate the first limb member relative to the second limb member;
identifying a gait phase of a gait cycle of a wearer of the powered prosthetic knee based at least in part on the sensor data; and
based at least in part on the identification of the gait phase, cause the recharging circuit to receive at least a portion of electrical energy from the electric actuator and supply at least some of the at least a portion of the electrical energy to the rechargeable battery to recharge the rechargeable battery.

Clause 24: The method of Clause 23, wherein gait phase of the wearer of the powered prosthetic knee comprises a real-time gait phase of the wearer of the powered prosthetic knee.

Clause 25: The method of any of the previous clauses, wherein the gait phase comprises at least a portion of Swing phase of the gait cycle.

Clause 26: The method of any of the previous clauses, wherein the gait phase comprises at least a portion of at least one of Initial swing of the gait cycle or Terminal swing of the gait cycle.

Clause 27: The method of any of the previous clauses, wherein the gait phase comprises at least a portion of at least two of Pre-swing, Initial swing, Mid swing, or Terminal swing.

Clause 28: The method of any of the previous clauses, wherein the gait phase of the gait cycle corresponds to at least one of a maximum extension of the powered prosthetic knee during the gait cycle or a maximum flexion of the powered prosthetic knee during the gait cycle.

Clause 29: The method of any of the previous clauses, wherein the gait phase of the gait cycle corresponds to an end of knee flexion during Initial swing of the gait cycle.

Clause 30: The method of any of the previous clauses, wherein the gait phase of the gait cycle corresponds to an end of knee extension during Terminal swing of the gait cycle.

Clause 31: The method of any of the previous clauses, wherein the gait phase of the gait cycle is a first gait phase of the gait cycle, wherein the method further comprises:
  identifying a second gait phase of the gait cycle of the wearer of the powered prosthetic knee based at least in part on the sensor data; and
  based at least in part on the identification of the second gait phase, causing the recharging circuit to electrically disconnect from the electric actuator.

Clause 32: The method of Clause 31, wherein upon the electrical disconnection of the recharging circuit from the actuator, the recharging circuit does not receive the electrical energy from the electric actuator.

Clause 33: The method of any of Clauses 31 or 32, wherein upon the electrical disconnection of the recharging circuit from the actuator, the recharging circuit does not supply the electrical energy to the rechargeable battery to recharge the rechargeable battery.

Clause 34: The method of any of Clauses 31 to 33, wherein the gait phase of the wearer of the powered prosthetic knee comprises a real-time gait phase of the wearer of the powered prosthetic knee.

Clause 35: The method of any of Clauses 31 to 34, wherein the second gait phase comprises at least a portion of a stance phase of the gait cycle.

Clause 36: The method of any of Clauses 31 to 35, wherein the second gait phase comprises at least a portion of the Swing phase of the gait cycle.

Clause 37: The method of any of Clauses 31 to 36, wherein the second gait phase comprises at least a portion of at least two of Pre-swing, Initial swing, Mid swing, or Terminal swing.

Clause 38: The method of any of Clauses 31 to 37, wherein the second gait phase comprises at least a portion of at least one of Initial swing of the gait cycle or Terminal swing of the gait cycle.

Clause 39: The method of any of Clauses 31 to 38, wherein the second gait phase comprises all portions of the gait cycle other than the first gait phase.

Terminology

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may include, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A powered prosthetic knee comprising:
   a first limb member;
   a second limb member;
   a rechargeable battery;
   an electric actuator coupled to the first limb member and the second limb member to form a joint, and electrically coupled to the rechargeable battery,
   wherein the electric actuator is configured to use energy received from the rechargeable battery to manipulate the first limb member relative to the second limb member to facilitate movement of the powered prosthetic knee,
   wherein during at least a portion of swing phase of a gait cycle, the electric actuator converts kinetic energy into first electrical energy that is greater than second electrical energy supplied to the electric actuator from the rechargeable battery;
   an enable/disable circuit located between the electric actuator and a recharging circuit;
   the recharging circuit comprising a reverse current protection circuit, wherein the reverse current protection circuit comprises a diode that prevents electrical energy from being supplied from the rechargeable battery to the recharging circuit, and wherein the recharging circuit is configured to:
      receive at least a portion of the first electrical energy from the electric actuator, and
      supply at least some of the at least a portion of the first electrical energy to the rechargeable battery to recharge the rechargeable battery;
   a power dissipation circuit located between the rechargeable battery and the electric actuator, the power dissipation circuit configured to dissipate at least some of the first electrical energy, wherein the power dissipation circuit comprises a brake chopper, and a switch in series with a resistor, wherein the brake chopper is configured to control the switch to allow at least some of the first electrical energy to dissipate across the resistor; and
   a controller configured to:
      determine an anticipated gait phase of the powered prosthetic knee based on a determined current gait phase and a determined cadence of a wearer, and
      selectively adjust the enable/disable circuit between an open circuit configuration and a closed circuit configuration to enable or disable the recharging circuit based at least in part on the anticipated gait phase, wherein the controller is configured to adjust the enable/disable circuit to the closed circuit configuration in response to a predicted time at which the powered prosthetic knee is predicted to begin the anticipated gait phase, and wherein the controller is configured to adjust the enable/disable circuit to the open circuit configuration in response to a predicted time at which the powered prosthetic knee is predicted to end the anticipated gait phase.

2. The powered prosthetic knee of claim 1, wherein the at least a portion of the swing phase of the gait cycle comprises at least a portion of at least one of an initial swing phase or a terminal swing phase.

3. The powered prosthetic knee of claim 1, wherein the at least a portion of the swing phase of the gait cycle comprises at least a portion of at least two of pre-swing, initial swing, mid swing, or terminal swing.

4. The powered prosthetic knee of claim 1, wherein the at least a portion of the swing phase of the gait cycle comprises at least a portion of the gait cycle corresponding to at least one of a maximum extension of the powered prosthetic knee or a maximum flexion of the powered prosthetic knee.

5. The powered prosthetic knee of claim 1, wherein the first electrical energy corresponds to counter electromotive force (EMF) induced by the electric actuator, and wherein the second electrical energy corresponds to a voltage of the rechargeable battery.

6. The powered prosthetic knee of claim 1, wherein the recharging circuit further comprises of a buck converter that is configured to down-convert a voltage and up-convert a current of the at least some of the at least a portion of the first electrical energy supplied to the rechargeable battery.

7. The powered prosthetic knee of claim 1, wherein the recharging circuit is further configured to control an amount of current or voltage supplied to the rechargeable battery.

8. A regenerative power system for a powered prosthetic knee, the system comprising:
  a recharging circuit electrically coupled to a rechargeable battery and further electrically coupled to an electric actuator that uses energy received from the rechargeable battery to manipulate a first limb member relative to a second limb member to facilitate movement of the powered prosthetic knee, wherein during at least a portion of swing phase of a gait cycle of a wearer of the powered prosthetic knee the electric actuator converts kinetic energy into first electrical energy that is greater than second electrical energy supplied to the electric actuator from the rechargeable battery, wherein the recharging circuit is configured to:
    receive at least a portion of the first electrical energy from the electric actuator, and
    supply at least some of the at least a portion of the first electrical energy to the rechargeable battery to recharge the rechargeable battery;
  an enable/disable circuit located between the recharging circuit and the rechargeable battery;
  a first reverse current protection circuit located between the rechargeable battery and the recharging circuit;
  a second reverse current protection circuit located between the rechargeable battery and the electric actuator, wherein the second reverse current protection circuit comprises an in-rush current limiter; and
  a controller configured to:
    selectively enable or disable the recharging circuit based at least in part on the first electrical energy, wherein the controller enables the recharging circuit based at least in part on a determination that the first electrical energy satisfies an energy threshold, and wherein the controller disables the recharging circuit based at least in part on a determination that the first electrical energy fails to satisfy the energy threshold.

9. The system of claim 8, wherein the at least a portion of the swing phase of the gait cycle comprises at least a portion of at least one of initial swing or terminal swing.

10. The system of claim 8, wherein the at least a portion of the swing phase of the gait cycle comprises at least a portion of at least two of pre-swing, initial swing, mid swing, or terminal swing.

11. The system of claim 8, wherein the at least a portion of the swing phase of the gait cycle comprises at least a portion of the gait cycle corresponding to at least one of a maximum extension of the powered prosthetic knee or a maximum flexion of the powered prosthetic knee.

12. The system of claim 8, wherein the first electrical energy corresponds to counter electromotive force (EMF) induced by the electric actuator, and wherein the second electrical energy corresponds to a voltage of the rechargeable battery.

13. The system of claim 8, wherein the recharging circuit further comprises of a buck converter that is configured to down-convert a voltage and up-convert a current of the at least some of the at least a portion of the first electrical energy supplied to the rechargeable battery.

14. The system of claim 8, further comprising a power dissipation circuit configured to dissipate at least some of the first electrical energy, wherein the power dissipation circuit comprises a brake chopper, a switch, and a resistor, wherein the brake chopper is configured to control the switch to allow at least some of the first electrical energy to dissipate across the resistor.

15. The system of claim 14, wherein the in-rush current limiter limits an amount of current being supplied from the rechargeable battery to the power dissipation circuit.

16. The system of claim 8, wherein the controller is further configured to selectively enable or disable the recharging circuit based at least in part on a state of charge of the rechargeable battery, wherein the controller disables the recharging circuit in response to a determination that the state of charge of the rechargeable battery satisfies a threshold state of charge.

17. The system of claim 8, wherein the first reverse current protection circuit comprises a diode that prevents electrical energy from being supplied from the rechargeable battery to the recharging circuit.

* * * * *